United States Patent [19]

Yoshie et al.

[11] Patent Number: 5,714,617
[45] Date of Patent: Feb. 3, 1998

[54] PROCESSES FOR PRODUCING A SALT OF N-GUANIDINO THIOUREA AND 3-AMINO-5-MERCAPTO-1,2,4-TRIAZOLE

[75] Inventors: Takehiko Yoshie, Uozu; Masanori Sasaki, Shinagawa-ku; Hiroshi Shibafuchi, Uozu; Yasushi Imai, Omiya; Masahiro Murotani, Toyama; Kenichi Ishii; Hajime Mura, both of Uozu, all of Japan

[73] Assignee: Nippon Carbide Kogyo Kabushiki Kaisha, Toyama, Japan

[21] Appl. No.: 609,573

[22] Filed: Mar. 1, 1996

Related U.S. Application Data

[62] Division of Ser. No. 357,807, Dec. 16, 1994, Pat. No. 5,559,243.

[30] Foreign Application Priority Data

Dec. 13, 1994 [JP] Japan ............................. 6-308862

[51] Int. Cl.[6] ................................................. C07D 249/12
[52] U.S. Cl. ........................... 548/263.8; 564/18; 564/227
[58] Field of Search ................... 564/18, 227; 548/263.8

[56] References Cited

U.S. PATENT DOCUMENTS

| 4,518,598 | 5/1985 | Hayes et al. ............................. 514/212 |
| 4,670,448 | 6/1987 | Clitherow et al. ....................... 514/334 |

FOREIGN PATENT DOCUMENTS

| 1960981 | 12/1969 | Germany . |
| 59-124333 | 7/1984 | Japan . |
| 5-247004 | 9/1993 | Japan . |
| 6-41096 | 2/1994 | Japan . |
| 1002291 | 3/1983 | U.S.S.R. . |
| 885575 | 12/1961 | United Kingdom . |

OTHER PUBLICATIONS

Ann. Univ. Mariae 1980 Curie–Sklodowska Sect. AA: Chem., vol. Data 1980, 35.

*Primary Examiner*—Richard L. Raymond
*Attorney, Agent, or Firm*—Pennie & Edmonds

[57] ABSTRACT

A method for producing 3-amino-5-mercapto-1,2,4-triazole, useful as an intermediate compound for a medicine or pesticide, or the intermediate thereof, a salt of N-guanidino thiourea from aminoguanidine thiocyanate or a thiocyanate and an aminoguanidine compound in the presence of an acid in a polar solvent, or even from hydrazine and cyanamide is disclosed.

2 Claims, 2 Drawing Sheets

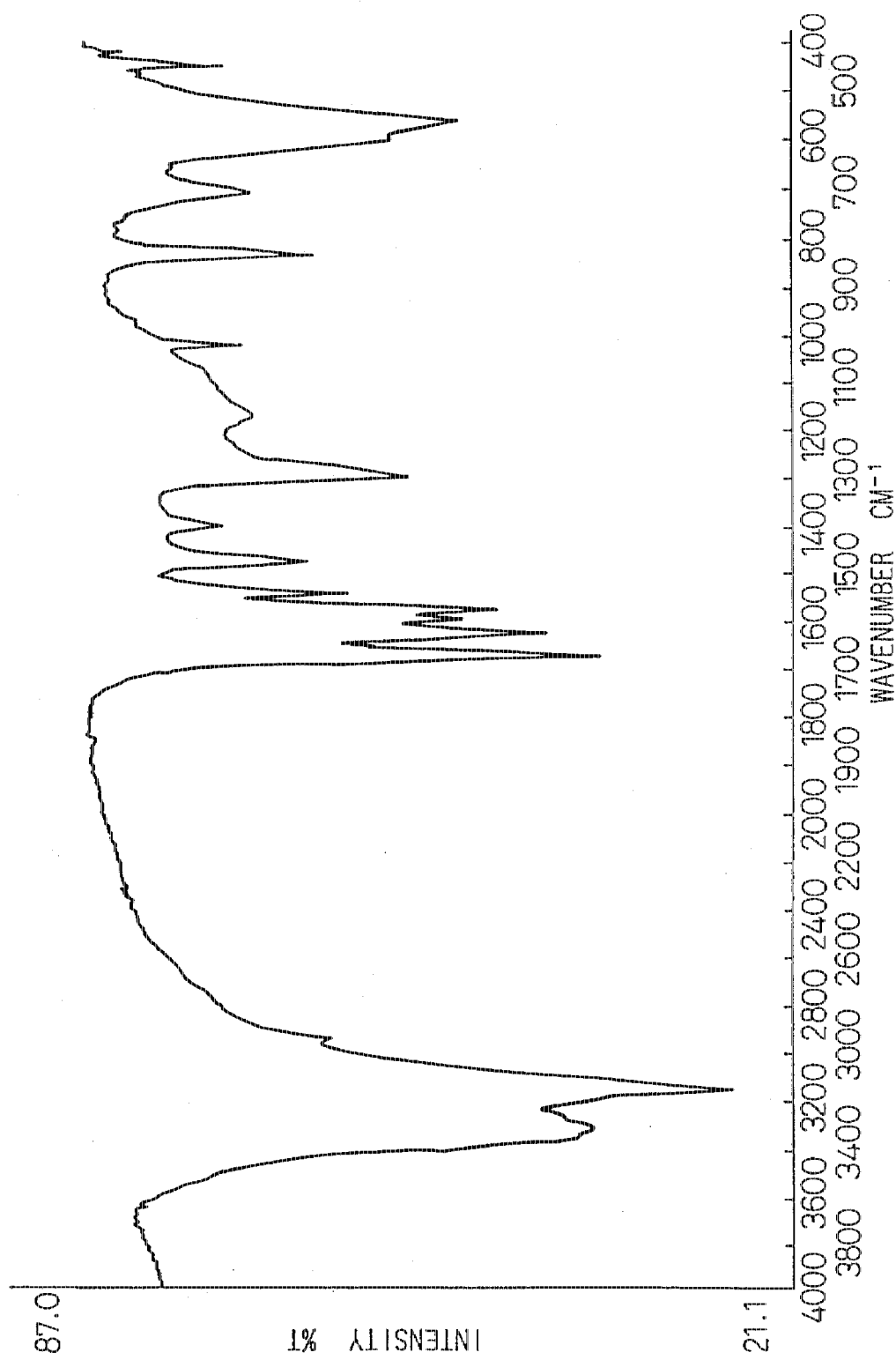

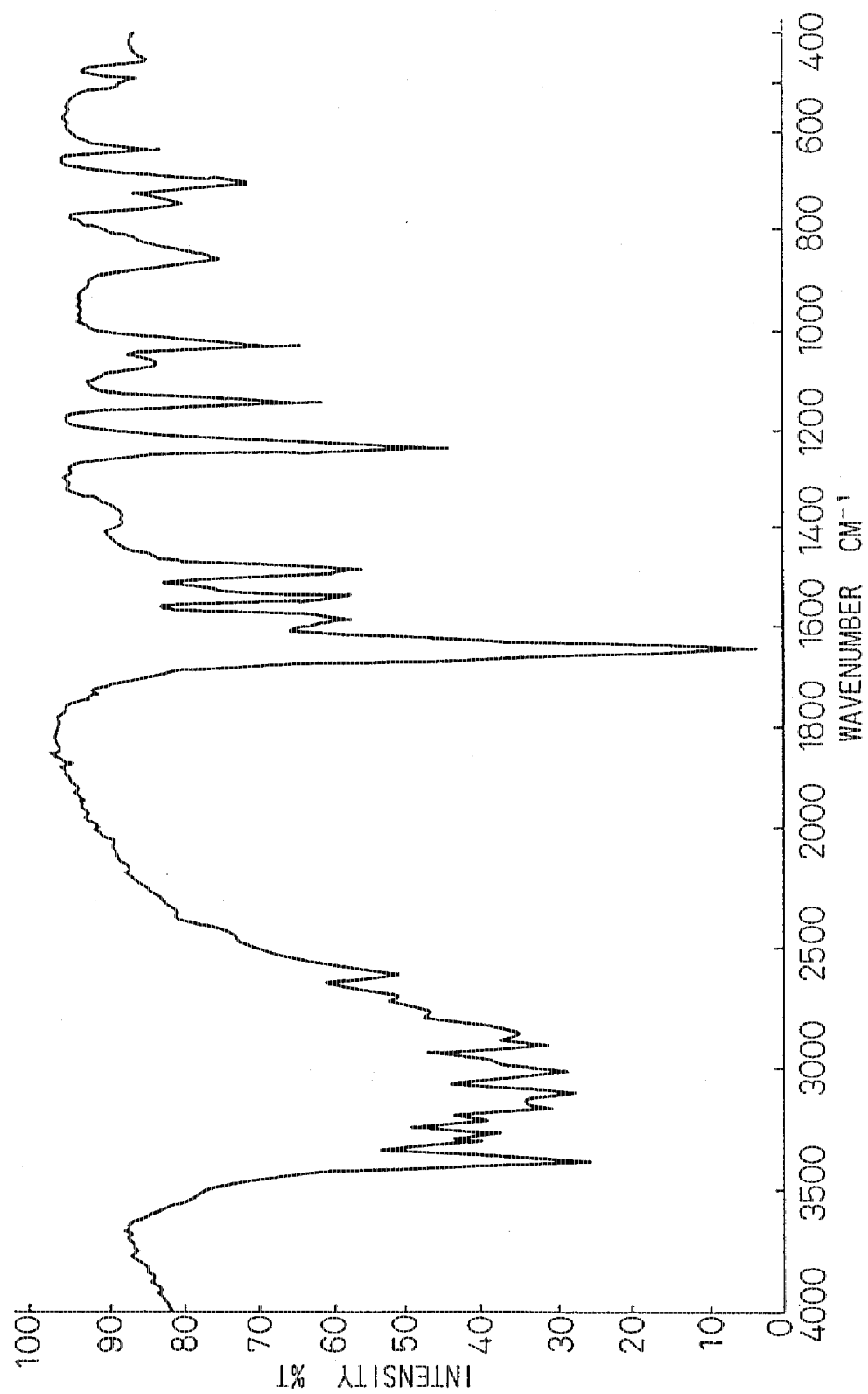

PROCESSES FOR PRODUCING A SALT OF N-GUANIDINO THIOUREA AND 3-AMINO-5-MERCAPTO-1,2,4-TRIAZOLE

This is a division of application Ser. No. 08/357,807, filed Dec. 16, 1994, now U.S. Pat. No. 5,559,243.

BACKGROUND OF THE INVENTION

1. Field of the Invention

The present invention relates to processes for producing a salt of N-guanidino thiourea and 3-amino-5-mercapto-1,2,4-triazole, which are useful as intermediate materials for medicines and pesticides. More specifically, it relates to a process for a salt of N-guanidino thiourea (i.e., "GTU salt"), which is an intermediate for 3-amino-5-mercapto-1,2,4-triazole (i.e., "ASTA"), by reacting, while heating, (i) a compound having both a thiocyanate group and an aminoguanidino group, or (ii) (a) a compound having a thiocyanate group and (b) a compound having an aminoguanidino group, in the presence of an acid, while heating, in a polar solvent. Furthermore, the resultant GTU salt can be converted to ASTA by heating the same under alkaline conditions.

2. Description of the Related Art

Several processes for producing ASTA are already known in the art. For example, DE-A-1960981 proposes a process for producing ASTA by dissolving aminoguanidine bicarbonate in ethanol containing acetic acid dissolved therein, followed by charging gaseous carbon disulfide thereto, after adding triethylamine, as follows.

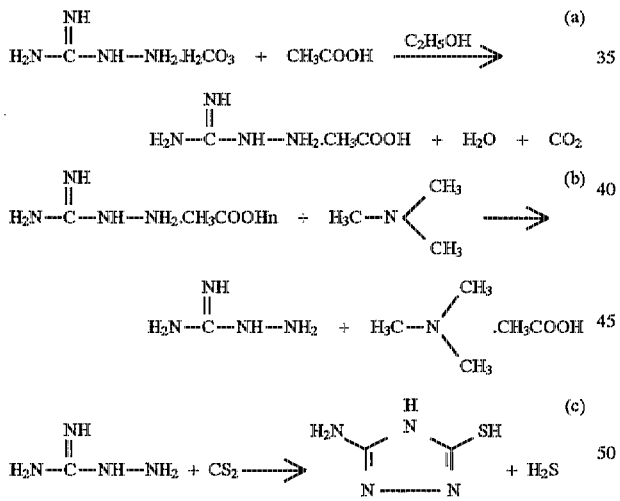

However, this process has the problems that the carbon disulfide reagent is toxic, flammable and explosive, and therefore, the production plant becomes expensive because special precautions must be taken in the apparatus (for example, the use of closed or sealed apparatus and the installation of means for treatment of exhaust gases and waste water, etc.).

U.S.S.R. Patent No. 1002291 proposes the synthesis of ASTA by reacting aminoguanidine hydrochloride and thiourea in a molten state in the absence of a solvent as follows.

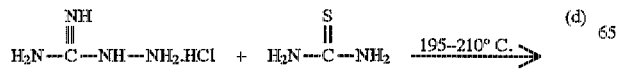

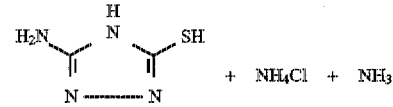

However, this process also has the problems that the reaction yield is not satisfactory. In addition, the starting thiourea is said to be toxic and carcinogenic, and therefore, the production plant becomes expensive.

Further, JP-A-59-124333 discloses a process for producing ASTA by reacting, while heating, GTU hydrochloric salt by dissolving the same in an aqueous sodium hydroxide. However, this publication does not disclose a method for preparing GTU. Furthermore, the present inventors proposed in JP-A-5-247004 the preparation of ASTA is prepared by reacting, in the absence of a solvent, aminoguanidine thiocyanate, or a salt of aminoguanidine and a salt of thiocyanic acid. However, this process still has the problems that the reaction rate and yield are not commercially satisfactory.

SUMMARY OF THE INVENTION

Accordingly, the objects of the present invention are to eliminate the above-mentioned problems of the conventional processes and to provide a novel process for industrially producing GTU salts and ASTA at a high yield and at a low cost.

Other objects and advantages of the present invention will be apparent from the following description.

In accordance with the present invention, there is provided a process for producing a salt of N-guanidino thiourea comprising the step of allowing to react (i) a compound having both a thiocyanate group and an aminoguanidino group, or (ii) (a) a compound having a thiocyanate group and (b) a compound having an aminoguanidino group, in the presence of an acid while heating in a polar solvent.

In accordance with the present invention, there is also provided a process for producing 3-amino-5-mercapto-1,2,4-triazole comprising the steps of (1) allowing to react (i) a compound having both a thiocyanate group and an aminoguanidino group, or (ii) (a) a compound having a thiocyanate group and (b) a compound having an aminoguanidino group, in the presence of an acid while heating in a polar solvent, to thereby form a reaction mixture containing a salt of N-guanidino thiourea; and (2) allowing to react the resultant reaction mixture in the step (1) under alkaline conditions, while heating.

In accordance with the present invention, there is further provided a process for producing a salt of N-guanidino thiourea comprising the steps of:

(1) allowing to react hydrazine and cyanamide in the presence of acid in a polar solvent, while heating to thereby obtain aminoguanidine;

(2) allowing to react the resultant aminoguanidine with a salt of thiocyanic acid in the presence of an acid in a polar solvent, while heating.

In accordance with the present invention, there is further provided a process for producing 3-amino-5-mercapto-1,2,4-triazole comprising the steps of:

(1) allowing to react hydrazine and cyanamide in the presence of an acid in a polar solvent, while heating to thereby obtain aminoguanidine;

(2) allowing to react the resultant aminoguanidine with a salt of thiocyanic acid in the presence of an acid in a polar solvent, while heating, to thereby form a salt of N-guanidino thiourea; and further (3) allowing to react the resultant salt of N-guanidino thiourea under alkaline conditions, while heating.

BRIEF DESCRIPTION OF THE DRAWINGS

The present invention will be better understood from the description set forth below with reference to the accompanying drawings, wherein:

FIG. 1 is an IR spectrum of the hydrochloric acid of N-guanidino thiourea obtained in Example 1, which is an intermediate of 3-amino-5-mercapto-1,2,4-triazole; and FIG. 2 is an IR spectrum of 3-amino-5-mercapto-1,2,4-triazole obtained in Example 2.

DESCRIPTION OF THE PREFERRED EMBODIMENTS

The present invention will now be described in more detail.

In the first step reaction for producing GTU salts, (i) compounds having both a thiocyanate group and an aminoguanidino group, or (ii) (a) compounds having a thiocyanate group and (b) compounds having an aminoguanidino group, are allowed to react in the presence of an acid, while heating, in a polar solvent.

Typical examples of a compound having both a thiocyanate group and an aminoguanidino group are aminoguanidine thiocyanate. Examples of a compound having a thiocyanate group, usable in the present invention, are ammonium thiocyanate, potassium thiocyanate, sodium thiocyanate, lithium thiocyanate, calcium thiocyanate, magnesium thiocyanate, barium thiocyanate. Among these, the use of ammonium isothiocyanate is industrially preferable because of its good process operability and easy availability.

Examples of a compound having an aminoguanidino group, usable in the present invention, are aminoguanidine hydrochloride, aminoguanidine sulfate, aminoguanidine nitrate, aminoguanidine bicarbonate, and aminoguanidine hydrobromide. Among these, the use of aminoguanidine bicarbonate is industrially preferable because of its good processability and easy availability.

When ammonium thiocyanate is used as the compound having a thiocyanate group, for example, and aminoguanidinobicarboxylic acid is used as the compound having an aminoguanidino compound for example, these compounds can be first reacted while heating in a polar solvent in the absence of an acid to obtain aminoguanidine thiocyanate by, for example, distilling off the formed ammonia and carbon dioxide, together with water, and the resultant aminoguanidine thiocyanate can be allowed to react in the presence of an acid, as desired.

The acids usable in the first step of the present invention are not specifically limited and preferably include inorganic acids such as hydrochloric acid, sulfuric acid, nitric acid, phosphoric acid, etc. These can be used alone or in any mixture thereof. The use of hydrochloric acid or sulfuric acid is preferable because of their good reactivity and easy availability.

The polar solvents usable in the present invention preferably include, for example, water and lower aliphatic alcohols having 1 to 3 carbon atoms, such as, for example, methyl alcohol, ethyl alcohol, iso-propyl alcohol. The use of water is most preferable.

The first step reaction of the present invention is considered to proceed as shown in the following reaction (1) or (2):

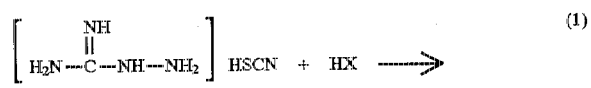

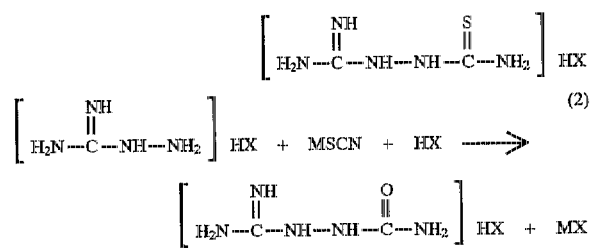

In the reactions (1) and (2), X represents a residual group of the acid.

As is clear from the above-reaction schemes (1) and (2), one equivalent of the thiocyanate group and one equivalent of the acid are necessary, based upon one equivalent of the guanidine group. Nevertheless, from the viewpoints of the desirable reactivity, the use of, preferably 1 to 5 equivalents, more preferably 1 to 2 equivalents, of the thiocyanate group and the use of, preferably 1 to 10 equivalents, more preferably 1 to 3 equivalents, most preferably 1 to 2 equivalents, of the acid are desirable, both based upon 1 equivalent of the guanidine group.

The acid can be used in any manner, and the manner of using the acid is not specifically limited. If necessary, the acid can be added to the reaction system by diluting with water to an appropriate concentration.

The reaction is generally carried out at a temperature of 50° C. or more, preferably at a temperature of 80° C. to 120° C. from the viewpoints of the reaction rate, the decomposition of the starting materials and the resultant GTU and the suppression of side reactions.

Although there are no specific limitations to the reaction time, the preferable reaction time is 5 minutes to 4 hours, preferably 10 minutes to 3 hours.

After the reaction is terminated, the resultant reaction mixture is optionally concentrated and cooled to precipitate the GTU salt, which is the intermediate the desired compound ASTA according to the present invention, followed by filtering. Thus, the crystal of the desired GTU salt can be obtained. Since the GTU salt has a certain water-solubility, a considerable amount of the GTU salt is dissolved in the filtrate. However, when the filtrate is recycled, the yield of the GTU salt can be improved.

The type of the salt of the GTU salt depends on the acid used in the first step reaction, and therefore, the examples thereof are the salt of the above-mentioned inorganic acids such as hydrochloric acid, hydrobromic acid, sulfuric acid, nitric acid and phosphoric acid. The preferable salts are the hydrochloride and sulfate, especially the hydrochloride.

In the second step of the present invention, the desired compound ASTA can be produced by dissolving the GTU salt obtained in the above-mentioned manner in the polar solvent as mentioned above, then making the resultant GTU solution alkaline by adding, for example, an alkaline compound, followed by reacting under heating. Alternatively, the reaction mixture obtained in the above-mentioned first step reaction can be directly used, without separating the salt of GTU after completing the first step reaction, as the starting GTU solution for the second step reaction.

The second step reaction of the present invention is considered to proceed as in the following reactions (3) and (4):

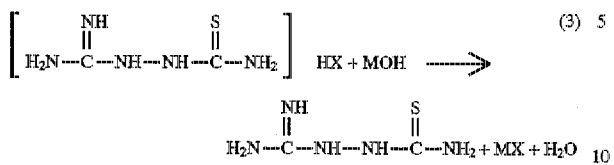

wherein M represents a univalent metal and X represents a residual group of the acid.

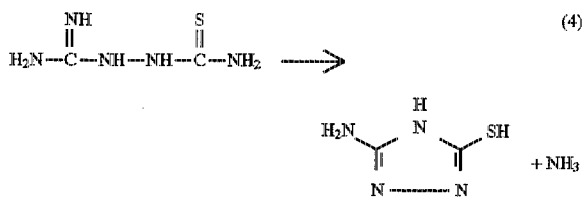

Examples of the above-mentioned alkaline compounds are hydroxides of alkali metals such as sodium hydroxide, potassium hydroxide and lithium hydroxide.

As the method for using the alkali compounds, it is preferable that the alkali compounds can be dropwise added to the reaction system by diluting the same to an appropriate concentration with, for example, water. The pH of the reaction mixture is preferably 7 to 14, more preferably 9 to 13.

Although there are no specific limitations to the reaction time, the reaction time is preferably 10 minutes to 6 hours, more preferably 1 to 2 hours.

After the reaction is completed, the desired ASTA can be obtained at a high purity by adjusting the pH of the resultant reaction mixture with an above-exemplified acid such as hydrochloric acid. When a further purified product is desired, the resultant product can be purified by, for example, column chromatography or acidlysis (or acid precipitation).

As the acidlysis, the resultant ASTA obtained as mentioned above is first dissolved in an aqueous solution of an alkali metal hydroxide (e.g., sodium hydroxide) to form an aqueous solution of an alkali metal salt of ASTA. The insoluble impurities such as sulfur are separated by filtration under vacuum, followed by drying to obtain the desired ASTA crystal at a 85–100% purity.

In accordance with the other embodiment of the present invention, the desired GTU salts and ASTA can be produced from hydrazine and cyanamide, both of which are easily available at an industrial scale.

That is, the GTU salt can be produced by reacting hydrazine (usually hydrate) and cyanamide in the presence of an acid in a polar solvent, while heating to thereby obtain aminoguanidine, followed by reacting the resultant aminoguanidine with a salt of thiocyanic acids in the presence of an acid in a polar solvent, while heating (e.g., 50° C. to reflux temperature), as shown in the following reactions (5), (6) and (7).

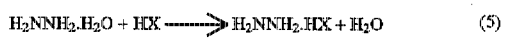

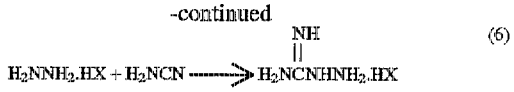

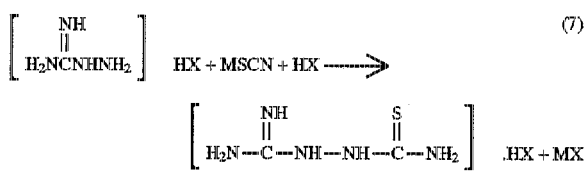

wherein X represents a residual group of the acid and M represents a metal ion or ammonium ion.

The acids, polar solvents and salts of thiocyanic acids usable in the above reactions are the same as those mentioned above. Although there are no limitations on the amounts of the acid and cyanamide, 0.9 to 1.5 mol of the acid and 1.0 to 1.5 mol of the cyanamide are preferably used in the reaction based upon 1 mol of the hydrazine. The preferable reaction time is 0.5 to 12 hours. The GTU salt can be recovered in the same manner as mentioned above.

According to the present invention, the aminoguanidine obtained in the reaction (6) can be directly reacted, without first recovering the same, or it can be first separated from the above reaction mixture, and then reacted, with thiocyanate to form GTU salt.

The GTU salt obtained above can be directly, or after separating, reacted to the desired ASTA, in the same manner as mentioned above.

EXAMPLE

The present invention will now be further illustrated by, but is by no means limited to, the following Examples.

EXAMPLE 1

To a 100 ml flask provided with a thermometer and an agitating means, 27.2 g (about 0.2 mol) of aminoguanidine bicarbonate, 15.2 g (about 0.2 mol) of ammonium thiocyanate, and 10 g of deionized water were charged. The mixture was heated in an oil bath until the temperature of the reaction mixture became 108° C., whereby the water, carbon dioxide and ammonia were distilled off.

Then, a reflux condenser was attached to the reaction flask. While the reaction mixture was heated to 95° C. while stirring, 28.0 g (about 0.27 mol) of 35% by weight hydrochloric acid was dropwise added over two hours, after which the temperature was maintained for one more hour. Thereafter, the reaction mixture was cooled to room temperature and the precipitated crystal was recovered by filtration. The wet crystal thus obtained was dried at 50° C. under a reduced pressure overnight. Thus, 16.3 g (about 0.11 mol) of the desired GTU hydrochloride crystal having a 91% purity was obtained. The melting point of the resultant GTU hydrochloride was 195°–197° C. Furthermore, its infrared (IR) spectrum is shown in FIG. 1. In addition, 9.3 g (about 0.07 mol) of the GTU hydrochloride was still dissolved in the filtrate, and therefore, the total yield of the GTU hydrochloride, together with the recovered crystal, was about 95% based upon the aminoguanidine bicarbonate.

EXAMPLE 2

Aminoguanidine bicarbonate, ammonium thiocyanate and deionized water were added to the same flask as used in Example 1 in the same amounts as in Example 10 The reaction mixture was heated in an oil bath in a similar manner as in Example 1 to distill off water, carbon dioxide and ammonia. Then, a reflux condenser was attached to the reaction flask and the reaction mixture was heated at 95° C. and 28.0 g (about 0.27 mol) of 35% hydrochloric acid solution was dropwise added over 2 hours, while heating and stirring as in Example 1. After the dropwise addition of the hydrochloric acid, the reaction mixture was allowed to stand at the same temperature for 1 hour to obtain the reaction mixture containing the GTU hydrochloride.

Then, to the reaction mixture, 18.3 g (about 0.23 mol) of 50% by weight aqueous solution sodium hydroxide solution was added to make the reaction mixture alkaline, and the mixture was reacted while refluxing (at about 110° C.) for 1.5 hours on an oil bath. After the completion of the reaction, the reaction mixture was cooled to room temperature, followed by adding 9.5 g of 35 wt % hydrochloric acid to adjust the reaction mixture to a pH of 1 to 2. The resultant precipitate of ASTA thus obtained was filtered to obtain 24.5 g of water-containing ASTA. The water-containing ASTA thus produced was dried at 50° C. under a reduced pressure overnight to obtain 19.2 g of the ASTA crystal having a purity of 97.1% (i.e., about 0.161 mol, yield of about 80.3% based on aminoguanidine bicarbonate). The decomposition temperature of the resultant ASTA was 298°–301° C., and its IR spectrum is shown in FIG. 2, and is approximately the same as that of the standard sample.

EXAMPLE 3

The production step of the reaction mixture containing the GTU hydrochloride in Example 2 was repeated except that 13.2 g (about 0.13 mol) of 98 wt % conc. sulfuric acid was used instead of 28.0 g (about 0.27 mol) of 35 wt % hydrochloric acid. Thus, 16.8 g of ASTA crystal (i.e., 0.138 mol, 70.5% yield based on the aminoguanidine bicarbonate) was obtained. The decomposition temperature thereof was 295°–299° C., which was substantially the same as that of the standard sample.

EXAMPLE 4

To a 5 liter separable flask provided with a thermometer and an agitating means, 1382 g (about 10 mol) of aminoguanidine bicarbonate, 767 g (about 10 mol) of ammonium thiocyanate and 500 g of deionized water were charged and the mixture was heated in an oil bath and water, carbon dioxide and ammonia were distilled off until the reaction temperature reached 108° C.

Then, a reflux condenser was attached to the reaction flask, and the reaction mixture was heated at 95° C., while stirring, and 1247 g (about 12 mol) of 35 wt % hydrochloric acid was dropwise added over 2 hours. The reaction was further maintained at the same temperature for one hour to obtain the reaction mixture containing the GTU hydrochloride.

To the resultant reaction mixture, 650 g (about 6.5 mol) of 40 wt % aqueous sodium hydroxide solution was then added to adjust the reaction mixture to an alkaline condition and the mixture was allowed to react in an oil bath under reflux (about 110° C.) for 1.5 hours. After the reaction was completed, the reaction mixture was cooled to room temperature, followed by adding 383 g of 35 wt % hydrochloric acid to adjust the pH thereof to 1–2. The resultant ASTA precipitate was separated by filtration to obtain 1296 g of the water-containing ASTA. The water-containing ASTA was dried at 50° C. under a reduced pressure overnight to obtain 935 g (about 7.71 mol, about 77.1% yield based on aminoguanidine bicarbonate). The decomposition temperature of the resultant ASTA was 295°–297° C. and the result of IR analysis was the same as shown in FIG. 2, both of which are substantially the same as those of the standard sample.

EXAMPLE 5

To a 500 ml flask provided with a thermometer, a reflux condenser and an agitating means, 51.2 g (0.505 mol) of hydrazine hydrate ($H_2NNH_2 \cdot H_2O$) and 46.7 g (0.46 mol) of 36 wt % hydrochloric acid were charged and the mixture was mixed while maintaining the temperature at 40° C., followed by adding 44.8 g (0.532 mol) of cyanamide thereto. The mixture was heated to 90° C. for 4 hours. Thus 51.8 g (93.8% yield, based on hydrazine hydrate) of aminoguanidine hydrochloride (AGH) was obtained.

To the reaction mixture obtained in the first step reaction above, 53.4 g (0.70 mol) of ammonium thiocyanate ($NH_4SCN$) was added and, by dropwise adding 71.6 g (0.706 mol) of 36 wt % hydrochloric acid thereto, the temperature of the reaction mixture was raised to allow to react while refluxing (at about 105° C.), followed by aging at 100° C. for 3 more hours. Thus, 71.5 g (84.4% yield) of N-guanidino thiourea hydrochloride was obtained.

To the reaction mixture obtained in the second step, 125 g (1.25 mol) of 40 wt % aqueous sodium hydroxide solution was carefully added and the mixture was reacted at a pH of 10.4 while refluxing (at about 105° C.,) for 4 hours. The reaction mixture thus obtained was allowed to cool to about 30° C. (pH=8.0), followed by dropwise adding 80.2 g (0.79 mol) of 36 wt % hydrochloric acid to adjust the pH thereof to 0.9. Thus, the precipitate of the desired ASTA was obtained.

The resultant precipitate of the crude ASTA was separated by filtration to obtain 55.3 g (0.37 mol, 73.5% yield, based on hydrazin hydrate) of the water-containing ASTA. The water-containing ASTA thus prepared was dissolved in 100 g of 20 wt % aqueous sodium hydroxide solution (pH=11.5), followed by filtration and washing with water. To the resultant filtrate, 50.6 g of 36 wt % hydrochloric acid was added to adjust the pH of the mixture to 5.9, followed by heating while refluxing at (105° C.) for 2 hours. The mixture was cooled to 25° C., 51.0 g of the purified ASTA thus obtained was dried at 80° C. under a pressure of 80 Torr overnight. Thus, 38.7 g (purity 99.5%, 0.33 mol, 66.4% yield based on hydrazine hydrate) of the purified ASTA was obtained. The decomposition temperature thereof was 297° to 300° C. and its IR spectrum is the same as that shown in FIG. 2, and both of these spectra are the same as that of a standard sample.

As explained above, according to the present invention, a salt of N-guanidino thiourea can be obtained from (i) a compound having both a thiocyanate group and an aminoguanidino group, or (ii) (a) a compound having a thiocyanate group and (b) a compound having an aminoguanidino group, none of which has been used in the prior art, in the presence of an acid, while heating, in a polar solvent, unlike the prior art processes.

Furthermore, according to the present invention, ASTA can be produced from (i) a compound having both a thiocyanate group and an aminoguanidino group, or (ii) (a) a compound having a thiocyanate group and (b) a compound having an aminoguanidino group, in the presence of an acid under heating in a polar solvent, followed by heating the resultant reaction mixture obtained above under alkaline conditions.

Furthermore, according to the present invention, the GTU salt and ASTA can be produced from hydrazine and cyanamide.

According to the present invention, the problems encountered in the prior art processes, namely the toxicity and the other dangerous properties of the starting materials and the cost increase due to the use of the various additional apparatus accompanied therewith as well as the unsatisfactory reaction yield can be advantageously solved and the desired compounds can be safely and inexpensively produced at an industrial scale.

We claim:

1. A process for producing a salt of N-guanidino thiourea comprising the steps of:

(1) allowing to react hydrazine and free cyanamide in the presence of hydrochloric acid in a polar solvent, while heating to thereby obtain aminoguanidine hydrochloride; and
   (2) directly reacting the resultant aminoguanidine hydrochloride contained in the reaction mixture obtained above with a salt of thiocyanic acid in the presence of an acid in a polar solvent, while heating, to form the salt.

2. The process of claim 1 which further comprises heating the resultant salt of N-guanidino thiourea under an alkaline condition to form 3-amino-5-mercapto-1,2,4-triazole.

* * * * *